United States Patent
McFadden

(10) Patent No.: US 9,583,663 B2
(45) Date of Patent: Feb. 28, 2017

(54) POWER SOURCE FOR AN ACCOMMODATING INTRAOCULAR LENS

(71) Applicant: NOVARTIS AG, Basel (CH)

(72) Inventor: Michael J. McFadden, Kennedale, TX (US)

(73) Assignee: Novartis AG, Basel (CH)

(*) Notice: Subject to any disclaimer, the term of this patent is extended or adjusted under 35 U.S.C. 154(b) by 5 days.

(21) Appl. No.: 14/526,739

(22) Filed: Oct. 29, 2014

(65) Prior Publication Data
US 2015/0179853 A1 Jun. 25, 2015

Related U.S. Application Data

(60) Provisional application No. 61/919,914, filed on Dec. 23, 2013.

(51) Int. Cl.
| | |
|---|---|
| H01L 31/055 | (2014.01) |
| H02S 40/38 | (2014.01) |
| A61F 2/16 | (2006.01) |
| H01L 31/054 | (2014.01) |

(52) U.S. Cl.
CPC ........ *H01L 31/055* (2013.01); *H01L 31/0547* (2014.12); *A61F 2/1624* (2013.01); *Y02E 10/52* (2013.01)

(58) Field of Classification Search
CPC .. A61F 2/1624; H01L 31/055; H01L 31/0547
USPC .................................................. 136/243–265
See application file for complete search history.

(56) References Cited

U.S. PATENT DOCUMENTS

| | | |
|---|---|---|
| 7,926,940 B2 | 4/2011 | Blum et al. |
| 2002/0196409 A1 | 12/2002 | Jani |
| 2012/0038841 A1 | 2/2012 | Taheri et al. |
| 2012/0099325 A1 | 4/2012 | Ghosh et al. |

OTHER PUBLICATIONS

PCT/US2014/062784; International Search Report, International Searching Authority, Jan. 29, 2015; 2 pgs.

*Primary Examiner* — Keith Hendricks
*Assistant Examiner* — Kourtney S Carlson

(57) ABSTRACT

A power supply including a luminescent solar concentrator (LSC) adapted for placement in an eye includes a base material transparent to visible light; and fluorescent particles doped within the base material. The fluorescent particles are capable of absorbing and reemitting light in the ultraviolet spectrum. A concentration of the fluorescent particles as a function of radius from an optical axis of the LSC is reduced in at least a portion of the base material outside of a pupil diameter. At least one photovoltaic cell is configured to receive the light in the ultraviolet spectrum trapped within the base material and to convert the trapped light into electricity.

7 Claims, 3 Drawing Sheets

POWER SOURCE FOR AN ACCOMMODATING INTRAOCULAR LENS

This application claims priority to U.S. Provisional Application No. 61/919,914 filed Dec. 23, 2013.

TECHNICAL FIELD

This invention relates generally to the field of accommodating intraocular lenses and, more particularly, to a power source for an accommodating intraocular lens.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquefies or emulsifies the lens so that the lens may be aspirated out of the eye. The diseased lens, once removed, is replaced by an IOL.

In the natural lens, distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. Furthermore, the ciliary muscle loses flexibility and range of motion. This makes it harder for the lens to focus on near objects, a medical condition known as presbyopia. Presbyopia affects nearly all adults upon reaching the age of 45 to 50. Various accommodative intraocular lenses (IDLs) have been proposed. One example is an electro-active optic. Electro-active IDLs may result in a refractive or diffractive optical power change. However, powering electro-active IDLs can be a considerable challenge, and there remains utility for improved power supplies.

SUMMARY OF THE INVENTION

Various embodiments of the present invention provide a power supply for an accommodating intraocular lens. In a particular embodiment, a power supply including a luminescent solar concentrator (LSC) adapted for placement in an eye includes a base material transparent to visible light; and fluorescent particles doped within the base material. The fluorescent particles are capable of absorbing and reemitting light in the ultraviolet spectrum. A concentration of the fluorescent particles as a function of radius from an optical axis of the LSC is reduced in at least a portion of the base material outside of a pupil diameter. At least one photovoltaic cell is configured to receive the light in the ultraviolet spectrum trapped within the base material and to convert the trapped light into electricity.

The embodiments discussed below are exemplary, and various changes can be made to these illustrative embodiments without deviating from the scope of the invention. For example, the features of one embodiment can be combined with those of another embodiment.

DETAILED DESCRIPTION

Figure 1:
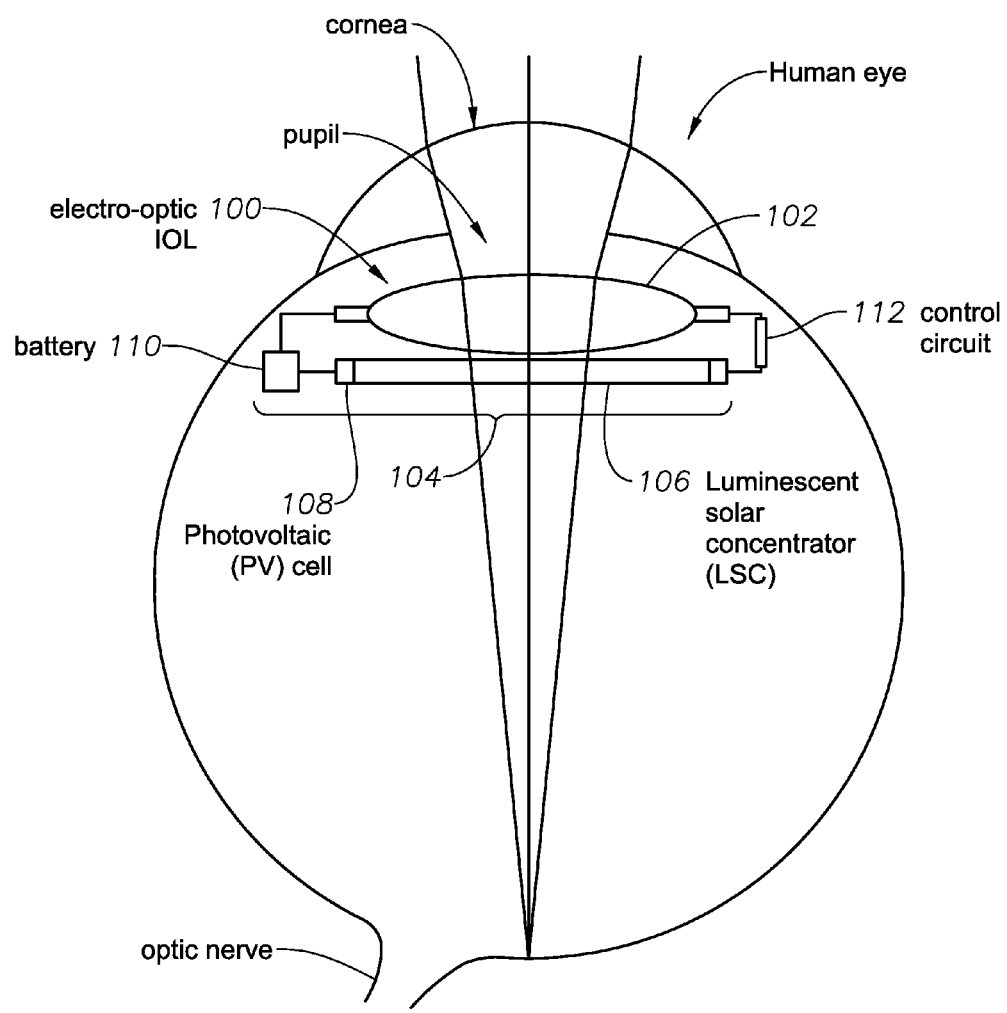
FIG. 1 schematically illustrates a top view of an electro-active IOL including a power supply according to a particular embodiment of the present invention.

As shown in FIG. 1, an electro-active accommodating intraocular lens (AIOL) 100 includes an electro-active optic 102 and a power supply 104. The power supply 104 includes a luminescent solar concentrator 106, photovoltaic cells 108, and a battery 110, which may also include any suitable electrical power storage device, such as a capacitor. The electro-active AIOL 100 likewise includes control circuitry 112, which further includes a sensor. The sensor generates a signal for the electro-active optic 102 indicative of accommodative demands, whether anatomical or manual. The signal, which may be binary (either accommodating or not), multi-step (e.g., near, far, and intermediate) or continuous, is received by the control circuitry 112, which controls the electro-active optic 102. The electro-active optic 102 may be any suitable electronic device that can change optical power in response to the signal from the sensor, including but not limited to liquid crystals, electromechanical optics, or any other suitable electro-active optical device. In particular embodiments, the sensor, control circuitry, electro-active optic 102 and power supply 104 may be packaged or encapsulated together within a biocompatible material for implantation.

The luminescent solar concentrator 106 is a device for collecting and intensifying solar radiation for power generation. Such devices are relatively well known for power generation, but they require adaptation for use in intraocular lenses. However, the eye constantly collects light, which is a potential power source. Specifically, the non-visible spectrum, including specifically ultraviolet radiation, is not used by the eye and can even be hazardous. The luminescent solar concentrator is designed to use this unwanted light for power generation, reducing the amount of ultraviolet light leaving the retina and providing additional power for the electro-active optic 102.

Figure 2:
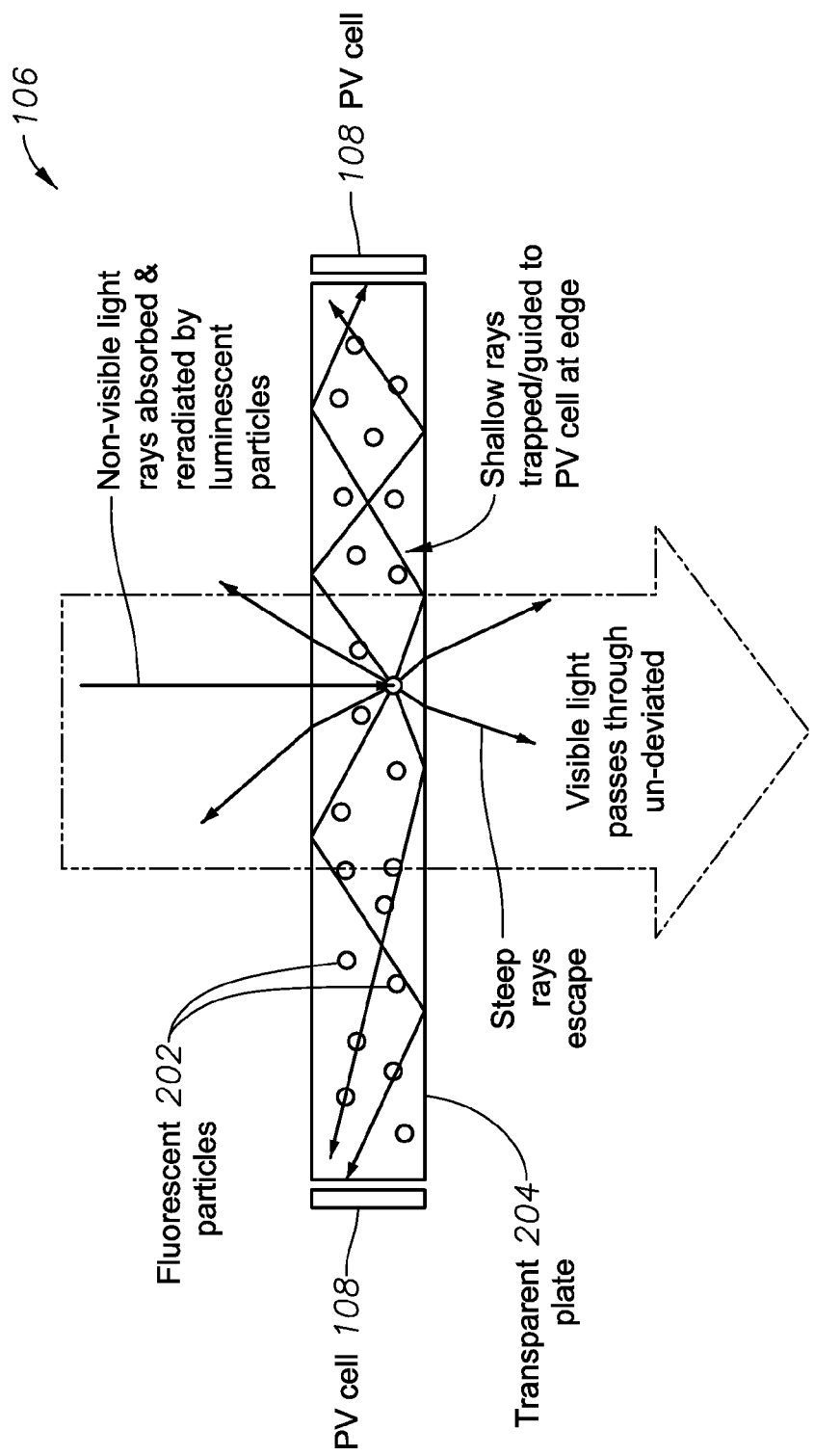
FIGS. 2 and 3 are top and anterior views, respectively, of the power supply of FIG. 1.

As shown in FIG. 2, the luminescent solar concentrator 106 includes fluorescent particles 202 doped in a base material 204 that is transparent to visible light. When incoming light rays 204 of UV radiation impinge on the fluorescent particles 202, the UV light is absorbed and reemitted in a variety of directions. The outer surface of the base material 204 of the luminescent solar concentrator reflects rays emitted at a sufficiently shallow angle by total internal reflection, allowing a significant portion of the incoming radiation to be contained within the base material 204. Advantageously, the outer surface of the base material 204 may be treated with a reflective coating to increase the probability of reflection for the UV light, which preferably will be transparent to visible light. The trapped UV light continues to be absorbed and reemitted by the fluorescent particles 202, with most of the light remaining trapped by total internal reflection until it is ultimately absorbed by photovoltaic cells 108, which in turn recharge the battery 110.

Figure 3:
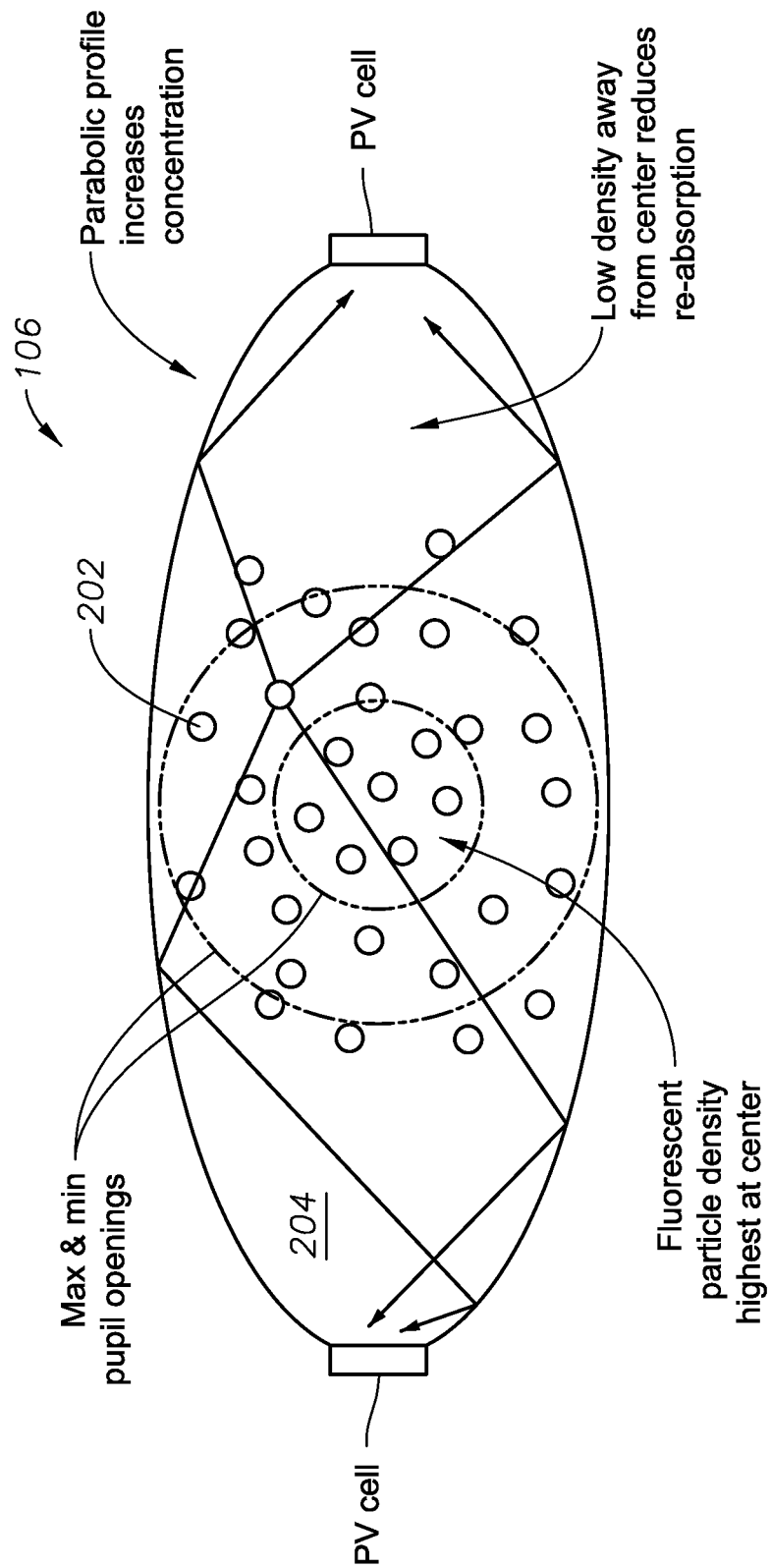

The anterior view of FIG. 3 illustrates additional features that assist the utility of the luminescent solar concentrator 106 in the optical application. The density of the fluorescent particles is increased in the optical zone of the electro-optical element 102, which allows an increased likelihood that incoming UV light will be scattered and trapped. Preferably, the high-concentration area of the fluorescent particles 102 extends to around the maximum pupil size of about 6 mm, which advantageously allows power collection under low-light conditions, when the light intensity is diminished but the pupil diameter is large. This may be referred to as the "collection zone," in that it represents the area where incoming UV light is being collected.

The concentration of the fluorescent particles 102 is lower outside the pupil diameter, where only the light that has already been trapped within the luminescent solar concentrator 106 is being retransmitted. This may be referred to as the "transmission zone," because this area is for transmitting the already-collected UV light within the luminescent solar concentrator 106. Because reabsorption allows light to be emitted at an angle that might allow it to escape, the concentration of fluorescent particles 102 is reduced in this area, which in turn increases the probability that captured light reaches the photovoltaic cells 104 while still allowing some rays that would otherwise escape to be absorbed. In the transmission zone, the outer edge of the housing 204 is likewise reshaped to increase the probability of total internal reflection, such as by forming a parabolic concentrator with a focus at the photovoltaic cell 108.

Although a specific embodiment has been disclosed for power an electro-active AIOL, it should be understood that those skilled in the art will recognize that the described power supply 104 could be implanted with conventional IOLs in the capsular bag and/or the sulcus of the eye and could be used for any powered implantable device by electrical or wireless connection. Thus, for example, powered pumps used for drug delivery or glaucoma treatment could be powered using such a power supply 104. Those having ordinary skill in the art will appreciate that various other changes can be made to the above embodiments without departing from the scope of the invention.

What is claimed is:

1. A power supply including a luminescent solar concentrator (LSC) adapted for placement in an eye, comprising:
   a base material having outer surfaces, the base material being transparent to visible light;
   fluorescent particles doped within the base material, the fluorescent particles being capable of absorbing and reemitting light in the ultraviolet spectrum, wherein a concentration of the fluorescent particles as a function of radius from an optical axis of the LSC is reduced in at least a portion of the base material outside of a pupil diameter; and
   at least one photovoltaic cell configured to receive the light in the ultraviolet spectrum trapped within the base material and to convert the trapped light into electricity.

2. The power supply of claim 1, wherein the portion of the base material with the reduced concentration of the fluorescent material is shaped as a parabolic concentrator with a focus at one of the at least one photovoltaic cells.

3. The power supply of claim 1, further comprising a battery coupled to the at least one photovoltaic cell.

4. The power supply of claim 3, further comprising an electro-optical element coupled to the battery.

5. The power supply of claim 4, wherein the power supply, the electro-optical element, and the battery are encapsulated together.

6. The power supply of claim 1, wherein at least a portion of the outer surfaces is covered by a coating to provide increased reflectance of ultraviolet light.

7. The power supply of claim 6, wherein the coating is transparent to visible light.

* * * * *